United States Patent [19]

Woodard

[11] 4,340,588
[45] Jul. 20, 1982

[54] BRUCELLOSIS VACCINE FOR CATTLE CONTAINING MYCOLATE ESTERS OF TREHALOSE

[75] Inventor: Lynn F. Woodard, Lewiston, Id.

[73] Assignee: Research Corporation, New York, N.Y.

[21] Appl. No.: 239,507

[22] Filed: Mar. 11, 1981

Related U.S. Application Data

[63] Continuation-in-part of Ser. No. 134,767, Mar. 28, 1980, abandoned.

[51] Int. Cl.[3] ...................... A61K 39/10; A61K 31/72

[52] U.S. Cl. ........................................ 424/92; 424/88; 424/180

[58] Field of Search ........................... 424/88, 92, 180; 536/115

[56] References Cited

U.S. PATENT DOCUMENTS

| | | | |
|---|---|---|---|
| 3,515,708 | 6/1970 | Williams et al. | 424/92 |
| 4,101,536 | 7/1978 | Yanomura et al. | 260/112.5 R |
| 4,152,423 | 5/1979 | Adams et al. | 424/92 |

OTHER PUBLICATIONS

Chemical Abstracts, vol. 91, p. 392, Abstract No. 87044t, 1979.

*Primary Examiner*—Blondel Hazel
*Attorney, Agent, or Firm*—Wyatt, Gerber, Shoup, Scobey & Badie

[57] ABSTRACT

Vaccine utilizing killed *Brucella abortus* strain 45/20 whole cells is useful for immunizing bovines. The vaccine contains trehalose dimycolate or an analog as an adjuvant.

4 Claims, No Drawings

BRUCELLOSIS VACCINE FOR CATTLE CONTAINING MYCOLATE ESTERS OF TREHALOSE

RELATED APPLICATIONS

This application is a continuation-in-part of copending application Ser. No. 134,767 filed Mar. 28, 1980 now abandoned.

BACKGROUND OF THE INVENTION

Recent increases in bovine brucellosis have raised serious doubts as to whether the disease can be eradicated using present techniques. While the conventional use of live strain 19 *Brucella abortus* vaccine has dramatically decreased the disease incidence over the past several decades, it now appears that either improved vaccines or improved diagnostic tests may be required to complete the eradication process.

We now know that there are two types of immunity involved in disease resistance. The first type of protection-humoral immunity-is afforded by antibodies in the circulation and body secretions. A second type of immunity is mediated by specialized whole blood cells (lymphocytes) and is thus deemed cell-mediated immunity (CMI). Recent studies have shown that cell-mediated rather than humoral immunity is involved in brucellosis resistance.

Many of the problems regarding brucellosis eradication arise from the fact that persistant antibody levels from the standard calfhood strain 19 vaccine interfere with laboratory techniques utilized in diagnosing naturally infected animals. Standard tube and plate agglutination tests record increased antibody titers which make it very undesirable to immunize adult cattle in infected herds, since immunized animals cannot be readily distinguished from infected animals. Also, the protection resulting from strain 19 vaccination is only 65–75% effective.

Strain 19 which stimulates both humoral immunity and CMI is especially undesirable for use in calves in certified-free areas or as an aid in the control of brucellosis in cows in heavily infected herds, due to false-positive titers.

Currently employed serological tests record the presence of humoral antibodies. It would be desirable therefore to add to the armamentarium of the veterinarian a vaccine which would stimulate the cell-mediated arm of the immune response without also stimulating circulating antibodies which react in the standard serologic tests employed at present. By stimulating only CMI, which is responsible for the clearance of intracellular parasites such as Brucella, present serological tests would indicate exposure or infection with naturally occurring *B. abortus* and not strain 19 or other vaccinal strains. Such a vaccine could also be used in adult cattle to control the disease in problem herds.

Vaccines comprising whole, killed *Brucella abortus* strain 45/20 (BA 45/20) cells, a rough strain, in inert oils such as paraffin oil or mineral oil have been used outside of the United States. These vaccines are not completely satisfactory for a number of reasons, principally because they require two initial doses followed by an annual booster injection (McDiarmid, *Ann Inst Pasteur* 102:792–800, and Hendricks et al, U.S. Department of Agriculture, Animal Health Division Staff Report, 1966). Additionally, adverse reactions at the site of innoculation commonly occur with some commercial water-in-oil vaccines.

Vaccines based on live cells, attenuated cells, killed cells and cellular antigens are currently used or have been reported. None are completely satisfactory. There is a genuine need for an improved vaccine which can be safely and reliably employed without the above-cited disadvantages.

THE INVENTION

Vaccines have now been discovered which avoid the aforesaid problems. They effect CMI and thus do not interfere with standard serological testing procedures by giving false-positive tests as a result of circulating antibodies arising from calfhood vaccinations. The vaccines of this invention comprise whole, killed *Brucella abortus* strain 45/20 (BA 45/20) cells together with a selected adjuvant. BA 45/20 is a rough strain.

The presently preferred adjuvants are at least one mono- or dimycolate of trehalose. These esters are a well known class of compounds comprising 6-mono- and 6,6-diesters of α,α-D-trehalose in which the esterifying group contains from 30 to 60 carbon atoms. They may be obtained from natural sources such as mycobacteria, corynebacteria and nocardia, or they may be synthesized. They may be represented by the formula:

wherein R and $R_1$ may be the same or different and selected from the group consisting of hydrogen and which is a mycolic acid moiety in which $R_2$ contains 30 to 90 carbon atoms, with the proviso that both R and $R_1$ cannot be hydrogen in a specific molecule. Mycolic acids are a well known and characterized class of compounds which are β-hydroxy-α-branched long chain fatty acids [Asselineau et al. Prog. Chem. Fats Other Lipids 16 59 (1978); Asselineau et al. Ann. Microbiol. (Paris) 129A 49 (9178); Lederer, E. Pure and Applied Chemistry 25, 135 (1971); Lederer, E. Springer Semin. Immunopathol. 2 133 (1979)].

The esters as obtained from natural sources such as those mentioned above, and strains of Arthrobacter and Brevibacterium are glycolipids and normally are mixtures in which the components are characterized by differing mycolic acids. The nomenclature employed in identifying these natural materials is somewhat imprecise. Generally those skilled in the art refer to relatively impure natural mixtures of trehalose dimycolates obtained from the above-cited sources as "cord factor". Normally cord factor contains about 90% dimycolate ester and 10% monomycolate ester with a small amount of extraneous material. Cord factors isolated from Mycobacteria spp. such as *M. tuberculosis, M. bovis* or *M. avium* and purified chromatographically using the method of Ribi et al. *J. Nat. Cancer Inst.* 52, 95 (1974)

and *Cell immunol.* 16, 11 (1975), are referred to as P3. This class of purified materials contains 95% to 99% dimycolates.

A specific P3 which is presently preferred for use in this invention is isolated chromatographically from cell walls of *Mycobacterium spp.* and is the third peak of the chromatographed free lipids, Ribi et al. *Annual of N.Y. Acad. of Sci.* 277, 228 (1976). It is available from the Rocky Mountain Laboratory, Hamilton, Mont.

The initials TDM are widely employed as a generic reference to trehalose dimycolates.

Cord factor from various sources has been shown to have a variety of physiological activities. However, prior to this invention, cord factor has not been known or suggested as an adjuvant in whole, killed vaccines.

Attempts to utilize soluble antigens from BA 45/20 to produce vaccines did not prove successful.

In this study, female Hartley guinea pigs weighing between 550 g and 750 g were randomly divided into principal and control groups of five animals. BA 45/20 whole cells were heat inactivated at 80° C. for one hour and the whole cells were ultrasonically disrupted in water. Cellular debris and insoluble materials was removed by centrifugation and the antigenic material precipitated with 10% (final concentration) trichloroacetic acid. The precipitate was dialyzed with distilled water and lyophilized.

Vaccines containing 300 µg of antigenic material together with 150 µg P3 in 0.1 ml of 1% oil in water emulsions were prepared.

Test animals were intradermally inoculated in the neck. Eight weeks later all animals were intramuscularly challenged with $1.04 \times 10^4$ colony forming units of *B. abortus* 2308. Two weeks after challenge, all animals were sacrificed and their spleens cultured for Brucella. Homogenized spleens were weighed and then diluted 1:5 (w/v) with 1.0% peptone in 0.5% slaine. Serial dilutions of each spleen were made into pour plates of trypticase-soy agar. Plates were incubated in 10% $CO_2$ at 37° C. for five days before Brucella colonies were counted. It was found that four out of the five test animals were infected and that all of the control animals were infected. It was observed also that none of the antigenic preparations were able to significantly reduce infection compared to non-vaccinated controls.

In contrast, with the vaccines of this invention, there was a significant reduction in infection. In these latter experiments, female Hartley guinea pigs (350 g–550 g) were employed. BA 45/20 strain was grown in trypticase-soy broth for five days at 37° C. and the bacteria inactivated by heating at 80° C. for one hour. Whole cells (WC) were collected by centrifugation, washed twice in saline, dialyzed against water and lyophilized. Vaccines comprising oil emulsions of WC and the preferred P3 described above (WC-P3) in 1% oil and Tween-saline were prepared to contain 300 µg WC and 150 µg P3 per 0.2 ml dose. Saline suspensions of WC free of P3 were also prepared at the same concentration.

Two groups of five animals each were inoculated in the neck with WC and WC-P3 vaccines respectively. Another group of five served as a control. Six weeks after inoculation, all animals were intramuscularly challenged with 5880 colony forming units of *B. abortus* 2308. Two weeks later, all animals were sacrificed and their spleens cultured as described above.

The results are shown in Table 1.

TABLE 1

IMMUNOGENIC CAPACITY OF WHOLE CELLS OF BA 45/20 IN VARIOUS ADJUVANTS

| Vaccine | No. Infected | Mean Brucella/Spleen | % Reduction |
|---|---|---|---|
| WC in saline | 5/5 | $2.8 \times 10^3$ | 52.5 |
| WC-P3 in oil | 3/5 | $3.60 \times 10^{1*}$ | 95.1 |
| Controls | 5/5 | $5.89 \times 10^3$ | — |

*$P < 0.05$

While these data show that there is some reduction with WC in saline, the reduction of WC-P3 in oil emulsion was dramatically higher.

Table 2 shows the results of a similar experiment in which various doses of adjuvant were employed. The result at an adjuvant dosage of 300 µg obviously represents an error in the experiment. It is given to be complete. The result at 1000 µg is also somewhat anomalous. It should be noted that the infection is of a low order.

TABLE 2

COMPARISON OF PROTECTION PROVIDED BY ADJUVANTED *B. ABORTUS* 45/20 VACCINES VARIOUS LEVELS IN GUINEA PIGS*

| Vaccine | Adjuvant Dosage (µg) | Average Splenic Wt. (gm) | Average Brucella/Spleen | Infected Total |
|---|---|---|---|---|
| WC-P3 in oil | 50 | 1.33 | $8.25 \times 10^3$ | 1/5 |
|  | 150 | 1.55 | 0 | 0/4 |
|  | 300 | 2.87 | $8.83 \times 10^5$ | 5/5 |
|  | 500 | 1.87 | 0 | 0/5 |
|  | 1000 | 1.25 | $2.41 \times 10^3$ | 3/5 |
| (Controls) |  | 9.54 | $1.8 \times 10^6$ | 20/20 |

*Challenged i.m. with $3.0 \times 10^4$ *B. abortus* 2308 at 7 weeks before sacrifice.

While the additives utilized in the process of this invention are referred to by the general term "adjuvants" for convenience, they do appear to have an immunostimulating effect which goes beyond such standard adjuvants as mineral and paraffin oils which are immunogenically inert.

The presently preferred embodiment of this invention comprises vaccines containing from 0.1 mg/ml to 5 mg/ml preferably 0.1 mg/ml to 1 mg/ml of killed BA 45/20 whole, killed cells and a P3 in weight ratio of from 1:1 to 20:1, preferably 1.0:1 to 2.25:1 in water and oil emulsion containing up to 2% by weight inert oil in water. There are several mono- and diesters of mycolic acids and trehalose and mixtures thereof which can also be employed.

The vaccine may be administered in immunologically effective dosage units which are usually from 0.1 to 5 ml. Normally oil in water emulsions will be employed, but with lower molecular weight adjuvants isotonic aqueous compositions can be employed. The oil may be either of mineral or vegetable origin. The vaccines may be administered by subcutaneous, intradermic, or intramuscular injections. They may also be administered by other routes, e.g. orally or rectally, or in the form of aerosols intended to come into contact with mucous membranes more especially ocular, nasal, respiratory or vaginal. Typically, one dose will provide sufficient immunity to protect against infection. However, second or even third booster treatments at one to twelve month intervals may be prudent.

The following non-limiting examples are given by way of illustration only.

EXAMPLE 1

1. Preparation of Whole cells
 a. Inoculate trypicase soy broth with *Brucella abortus* 45/20 bacteria.
 b. Incubate (37° C.) for 4–6 days and culture to insure purity.
 c. Heat kill (80° C. for 1 hour).
 d. Collect bacteria by centrifugation (10,000× g for 30 minutes).
 e. Wash twice in saline.
 f. Dialyze against water for 24 hours.
 g. Freeze-dry (lyophilize).
2. Preparation of WC-P3 Vaccine Place 1.5 mg of dried whole cells (approximately $5 \times 10^9$ bacteria) in Corning 7725 tissue grinder. Add 0.75 mg of P3 (dissolved in 95:5 chloroform methanol. Evaporate C:M under a laminer flow hood or $N_2$ gas. Warm vessel to 65° C. in a water bath and add 10 μl (0.01 ml) of refined mineral oil. Grind WC, P3 and oil for 1 minute at 1000 rpm with teflon pestle. Add 0.99 ml of Normal (0.9%) saline solution that contains 0.2% Tween 80 (an emulsifier). Grind an additional 3 minutes.

Guinea pig dose=0.2 ml (300 μg of WC+150 μg of P3).

EXAMPLE 2

The procedure of Example 1 was repeated except that P3 was replaced with the monoester of trehalose obtained by esterifying trehalose with nocardomycolic acid prepared by the procedure described in U.S. Pat. No. 4,101,536. It was used in 3 ml dosage units by intramuscular injection to immunize cattle against *Brucella abortus* infections.

EXAMPLE 3

The procedure of Example 1 was repeated except that P3 was replaced with trehalose dinocardomycolate obtained as in Example 2.

What is claimed is:

1. A vaccine comprising 0.1 mg/ml to 5 mg/ml of whole, killed *Brucella abortus* 45/20 cells together with a mono- or diester of trehalose as an adjuvant wherein the esterifying moiety is a mycolic acid containing from 30 to 90 carbon atoms in an immunologically acceptable carrier, the weight ratio of cells to adjuvant being from 1:1 to 20:1.

2. A product as in claim 1 wherein the ester is a monoester and the esterifying group is nocardomycolic acid.

3. A method of immunizing cattle against *Brucella abortus* infection which comprises administering to cattle to be immunized an immunologically effective dose of a vaccine comprising 0.1 mg/ml to 5 mg/ml of whole killed *Brucella abortus* 45/20 cells together with a mono- or diester of trehalose as an adjuvant wherein the esterifying moiety is a mycolic acid containing from 30 to 90 carbon atoms in an immunologically acceptable carrier, the weight ratio of cells to adjuvant being from 1:1 to 20:1.

4. A method as in claim 3 wherein the ester is a monoester and the esterifying group is nocardomycolic acid.

* * * * *